United States Patent [19]
Heinerman et al.

[11] Patent Number: 6,150,296
[45] Date of Patent: Nov. 21, 2000

[54] PROCESS FOR PREPARING A CATALYST SUITABLE FOR USE IN ISOMERIZING HYDROCARBONS, THE CATALYST THUS OBTAINED, AND ITS USE

[75] Inventors: Jacobus Johannes Leonardus Heinerman, Amsterdam; Petrus Josephus Mangnus, Leiden, both of Netherlands

[73] Assignee: Akzo Nobel NV, Arnhem, Netherlands

[21] Appl. No.: 09/082,533

[22] Filed: May 21, 1998

Related U.S. Application Data

[63] Continuation-in-part of application No. 08/746,321, Nov. 21, 1996, abandoned.

[30] Foreign Application Priority Data

Nov. 30, 1995 [EP] European Pat. Off. ............... 95203296

[51] Int. Cl.$^7$ ............... B01J 31/02; B01J 31/28; B01J 31/30; B01J 27/128; B01J 27/13
[52] U.S. Cl. ............ 502/152; 502/171; 502/229; 502/230; 502/231; 502/326; 502/327; 502/332; 502/333; 502/334
[58] Field of Search ................... 502/152, 171, 502/229, 230, 231, 326, 327, 332, 333, 334

[56] References Cited

U.S. PATENT DOCUMENTS

| | | |
|---|---|---|
| 3,903,195 | 9/1975 | Franck et al. |
| 3,928,383 | 12/1975 | Antos. |
| 5,654,254 | 8/1997 | Wu et al. ............... 502/334 |

FOREIGN PATENT DOCUMENTS

| | | |
|---|---|---|
| 952348 | 3/1964 | United Kingdom. |
| 1432639 | 4/1976 | United Kingdom. |

*Primary Examiner*—Elizabeth D. Wood
*Attorney, Agent, or Firm*—Oliff & Berridge, PLC

[57] ABSTRACT

A process for preparing an activated isomerization or alkylation catalyst composition in which a catalyst composition comprising a Group VIII noble metal and a hydrocarbon-substituted aluminum compound on an alumina carrier containing up to 20 wt. % of other components involves activating the catalyst by contacting the catalyst with a hydrogen-containing gas at a temperature in excess of 500° C., with the proviso that at least when the hydrocarbon-substituted aluminum compound present in the catalyst composition is not a hydrocarbon-substituted aluminum halide, the catalyst composition to be activated is contacted with a halogen compound either prior to or during the activating step. The catalyst obtainable by this process and the use thereof in hydrocarbon conversion processes, such as isomerization and alkylation processes, are also part of the invention. The effect of the high-temperature activation step is that the activity of the catalyst is improved in comparison with a catalyst of the same composition which has not been subjected to the high temperature activation step.

13 Claims, No Drawings

PROCESS FOR PREPARING A CATALYST SUITABLE FOR USE IN ISOMERIZING HYDROCARBONS, THE CATALYST THUS OBTAINED, AND ITS USE

The present application is a continuation-in-part application of U.S. patent application Ser. No. 08/746,321, filed Nov. 21, 1996 now abandoned. The entire disclosure of the prior application is hereby incorporated by reference in its entirety. The application claims priority of European Patent Application No. 95203296.9 filed on Nov. 30, 1995, and benefit of U.S. Provisional Application No. 60/009,405 filed on Dec. 4, 1995.

FIELD OF THE INVENTION

The invention pertains to a process for preparing an activated catalyst composition suitable for use in isomerizing hydrocarbons based on a catalyst composition comprising a Group VIII noble metal and a hydrocarbon-substituted aluminum compound on an alumina carrier containing up to 20 wt. % of other components, the catalyst thus obtained, and its use.

BACKGROUND OF THE INVENTION

Isomerization catalysts comprising a Group VIII noble metal and a hydrocarbon-substituted aluminum compound on an alumina carrier are known in the art, as are processes for the preparation thereof.

GB Patent 1 432 639 describes a process for preparing an isomerization catalyst of this description in which a composition comprising a Group VIII noble metal and alumina is contacted with a hydrocarbon-substituted aluminum halide, whereupon the resulting catalyst is used directly for isomerizing paraffins. GB Patent 952 348 describes a process for preparing an isomerization catalyst in which a composition comprising a Group VIII noble metal and alumina is contacted with a trialkyl aluminum compound, whereupon the whole is reacted with, e.g., a hydrogen halide at a temperature below 260° C. This treatment may be followed by a further activation with hydrogen at a temperature below 371° C. if so desired.

However, the catalysts described in these references fail to function in a satisfactory manner, and there is need for a catalyst of improved activity.

It has now been found that the activity of a catalyst composition comprising a Group VIII noble metal and a hydrocarbon-substituted aluminum compound on an alumina carrier containing up to 20 wt. % of other components can be enhanced by subjecting this composition to a high-temperature activation step in which the composition is contacted with a hydrogen-containing gas at a temperature of 500° C. or higher. In this respect it should be taken into account that if the hydrocarbon-substituted aluminum compound is not a hydrocarbon-substituted aluminum halide, it will be necessary to contact the catalyst composition to be activated with a halogen compound, either prior to or during the activation step.

SUMMARY OF THE INVENTION

The present invention generally relates to a process for preparing an activated catalyst composition suitable for use in isomerizing hydrocarbons based on a catalyst composition comprising a Group VIII noble metal and a hydrocarbon-substituted aluminum compound on an alumina carrier containing up to 20 wt. % of other components. The invention also relates to the catalyst obtained by such process and its use in isomerizing hydrocarbons.

DETAILED DESCRIPTION OF THE INVENTION

The present invention generally relates to a process for preparing an activated catalyst composition in which a catalyst composition comprising a Group VIII noble metal and a hydrocarbon-substituted aluminum compound on an alumina carrier containing up to 20 wt. % of other components is activated by contacting it with a hydrogen-containing gas at a temperature above 500° C., with the proviso that at least when the hydrocarbon-substituted aluminum compound present in the catalyst composition is not a hydrocarbon-substituted aluminum halide, the catalyst composition to be activated is contacted with a halogen compound either prior to or during the activating step.

The Group VIII noble metal present in the catalyst may be selected from the group of ruthenium, rhenium, palladium, osmium, iridium, and platinum, with preference being given to platinum, palladium, and mixtures thereof. The final catalyst preferably contains 0.01–2 wt. % of the Group VIII noble metal, calculated as metal, more particularly 0.05 to 1 wt. %. Other metal components may also be present in the catalyst composition if so desired. Examples of other metal components which may influence the activity, selectivity or stability of the catalyst are tin, lead, germanium, bismuth, cobalt, nickel, indium, gallium, zinc, uranium, thallium, zirconium, and mixtures thereof.

The alumina carrier containing up to 20 wt. % of other components preferably takes the form of particles, which are obtained by means of, e.g., extrusion, pelletizing, or by some other known method. The particles' shape may vary. As suitable shapes may be mentioned spheres, cylinders, rings, and symmetric or asymmetric polylobes, such as trilobes and quadrulobes. Generally, the particles will have a diameter in the range of 1 to 10 mm, and a length which is also in the range of 1 to 10 mm. The alumina may contain up to 20 wt. % of other constituents, such as silica, magnesia, titania, or zirconia. It is preferred that more than 90 wt. % of the carrier, more preferably over 95 wt. %, and most preferably substantially all of the carrier consists of alumina. Here, the term "substantially all" means that the catalyst carrier consists essentially of alumina, with the only additional carrier components being impurities which do not influence the properties of the catalyst. Suitable aluminas include the active aluminas such as gamma-alumina, eta-alumina, theta-alumina, and mixtures thereof. Gamma-alumina is particularly preferred.

The alumina carrier containing up to 20 wt. % of other components preferably has a surface area of 100–500 $m^2/g$, a total pore volume of 0.1–1 ml/g, and an average pore diameter of 2–20 nm.

The compositing of the metals components with the carrier may be in any manner known in the art. For example, one can start by preparing carrier particles by shaping a carrier precursor, for example by extrusion, and calcining the resulting shaped particles. The carrier particles can then be impregnated with an impregnating solution comprising a soluble salt or complex of the metal or metals to be provided. For example, one may impregnate the carrier with an impregnation solution containing chloroplatinic acid, platinum dichloride, platinum tetrachloride hydrate, etc. It is well-known in the art to add additional components to the impregnation solution to stabilize the solution, or to influence the distribution of metal over the catalyst carrier. For example, if a homogeneous platinum distribution is desired, a strongly acid impregnation solution, such as an impregnation solution containing chloroplatinic acid, HCl, and $HNO_3$, is commonly used. The impregnated particles may optionally be calcined.

On the other hand, it is also possible to mix compounds of the metal or metals to be incorporated into the catalyst composition with the carrier precursor, and then shape the mixture, for example by extrusion, after which the extrudates are calcined.

If so desired, the Group VIII metal component present on the carrier may be reduced, e.g., by passing hydrogen over the composition at a temperature in the range of 100 to 600° C.

The hydrocarbon-substituted aluminum compound used in the process according to the invention may be a halide, in which case a hydrocarbon-substituted aluminum chloride is preferably used. The hydrocarbon-substituted aluminum halide may be, e.g., a compound satisfying the formula $AlX_yR1_nR2_m$, wherein X is a halogen atom, R1 and R2 may be the same or different and are selected from alkyl groups or aryl groups having 1–12 carbon atoms, y has the value 1 or 2, and n and m have the value 0 or 1, with the sum of y, n, and m being 3. X may be selected from fluorine, chlorine, bromine, and iodine, and is preferably chlorine. R1 and R2 may be selected from, e.g., methyl, ethyl, isopropyl, butyl, phenyl, cyclohexyl, etc. Suitable hydrocarbon-substituted aluminum halides include diethyl aluminum chloride, methyl aluminum dichloride, ethyl aluminum dichloride, and isobutyl aluminum dichloride. It should be noted that the hydrocarbon-substituted aluminum halide also may be a mixture of various hydrocarbon-substituted aluminum halides or a complex, for instance an alkyl aluminum sesquichloride.

When the hydrocarbon-substituted aluminum compound is not a halide, it may satisfy the formula AlR1R2R3, wherein R1, R2, and R3 may be the same or different and are selected from alkyl groups or aryl groups having 1–12 carbon atoms, such as described above. Examples of hydrocarbon-substituted aluminum compounds include triethyl aluminum and isobutyl diethyl aluminum. Mixtures of various non-halide hydrocarbon-substituted aluminum compounds may also be used.

If so desired one may also apply a combination of one or more hydrocarbon-substituted aluminum halides with one or more non-halide hydrocarbon-substituted aluminum compounds. In that case, care should be taken that a sufficient amount of halide is added to the catalyst composition either with the hydrocarbon-substituted aluminum halide, or separately.

The hydrocarbon-substituted aluminum compound can be incorporated into the catalyst composition in an amount of 0.05 to 0.20 mole of hydrocarbon-substituted aluminum compound per mole of carrier. The hydrocarbon-substituted aluminum compound is incorporated into the catalyst composition in a manner known in the art. For example, it is possible to incorporate the hydrocarbon-substituted aluminum compound into the catalyst by contacting it with a composition comprising a Group VIII noble metal, optionally in the reduced form, on an alumina carrier containing up to 20 wt. % of other components. Although less preferred, it is also possible to first incorporate the hydrocarbon-substituted aluminum compound into the catalyst composition, and only then incorporate the Group VIII noble metal.

The incorporation of the hydrocarbon-substituted aluminum compound into the catalyst composition may take the form of the compound being dissolved in a solvent and impregnating the carrier, which optionally comprises the Group VIII noble metal component, with this solution, followed by removal of the solvent. Preferably, the boiling point of the solvent will not be too high, since it is harder to remove high-boiling solvents from the composition. Suitable solvents include pentane, hexane, heptane, etc. It should be noted in this context that the removal of the solvent from the solution prior to the activating step is not always required. One possible alternative is to evaporate the solvent during the activating step. Of course, the feasibility of this option is dependent upon the nature of the solvent and the other process conditions.

In the process for the activation of a catalyst composition according to the invention, a catalyst composition comprising a Group VIII noble metal and a hydrocarbon-substituted aluminum compound on a carrier is contacted with a hydrogen-containing gas at a temperature above 500° C., preferably in the range of 500 to 1000° C., more preferably in the range of 500 to 800° C., most preferably 600–750° C. The activation is carried out by contacting the catalyst with the hydrogen-containing gas over a period of 15 minutes to 5 hours, preferably of 30 minutes to 3 hours.

In the activating process, use is made of a hydrogen-containing gas which may contain other constituents if so desired, such as diluents, e.g., nitrogen, argon, or other inert gases. The hydrogen-containing gas used in the activation process according to the invention preferably holds less than 10 ppm of water and less than 10 ppm of oxygen or oxygen-containing components.

As indicated before, when the hydrocarbon-substituted aluminum compound is not a hydrocarbon-substituted aluminum halide, the catalyst composition should be contacted with a halogen compound, particularly a chlorine compound, either before or during the activation treatment. For instance, it is possible to first contact the catalyst composition with a halogen compound at a temperature in the range of 0 to 800° C., preferably in the range of 50 to 250° C., and then activate the catalyst with hydrogen at a temperature in excess of 500° C. It is also possible to carry out the activation in the presence of a halogen compound.

Examples of suitable halogen compounds to be used either before or in the activation step are hydrogen halides, such as hydrogen chloride, a halogen gas, a halogenated hydrocarbon, such as carbon tetrachloride, chloroform, chloroethane, etc. Hydrogen halides, particularly HCl, are generally preferred. If the activation step is carried out in the presence of a halogen compound, the molar ratio of the halogen compound to the hydrogen gas in the activation gas is preferably in the range of 0.1 to 10, more particularly in the range of 1 to 5. When the hydrocarbon-substituted aluminum compound is a hydrocarbon-substituted aluminum halide, it is possible to use either a hydrogen-containing gas which does not contain any halogen compounds or a hydrogen-containing gas which contains at least one halogen compound in the activating process.

Generally, the use of a hydrogen-containing gas which comprises a halogen compound will lead to a catalyst with a somewhat higher activity than the use of a hydrogen-containing gas which does not comprise a halogen compound. It is also possible to contact the catalyst composition comprising a hydrocarbon-substituted aluminum halide and the Group VIII metal with a halogen compound before the activation is carried out in the manner described above, but generally little benefit is derived from this. The final catalyst will generally contain up to 15 wt. % of halogen, which is preferably chlorine.

It is part of the common knowledge of the skilled person that isomerization catalysts are highly halogenated, more particularly chlorinated, as opposed to reforming catalysts, which have halogen contents of the order of 1 wt % only. Isomerization catalysts including those prepared by the process of the present invention preferably have halogen contents of at least 2.5 wt %, based on the total weight of the catalyst. More preferably, the final catalyst should contain at least 3.0 wt % halide, based on the total weight of the catalyst, and even more preferred is a halide content of the catalyst of at least 3.5 wt %, based on the total weight of the catalyst.

The required halogen content of the catalyst can be obtained by a proper selection of the amount of hydrocarbon-substituted aluminum halide and/or the amount of halogen compound applied in the preparation process of the present invention.

The activated catalyst prepared by the process according to the invention is suitable for use in a variety of hydrocarbon conversion processes. It can, for example, be used in the isomerization of aromatic and aliphatic hydrocarbons, more particularly for isomerizing n-paraffins having 4 to 12 carbon atoms. It is also suitable for isomerizing mixtures of different n-paraffins and mixtures of n-paraffins and aromatic hydrocarbons. The catalyst according to the invention produces particularly favorable results in the case of $C_4$, $C_5/C_6$, and $C_7$ isomerizations. Preferably, the feedstock to be isomerized contains at least 50 wt. % of paraffins to be isomerized. The feedstock may contain olefins, but preferably less than 10%, because the presence of olefins leads to increased hydrogen consumption. As is known in the art, the feed should be relatively free from sulphur components and water, because these materials act as catalyst poisons. The feed generally contains up to 1 ppm of sulphur, and up to 0.5 ppm of water.

The isomerization process may take the form of the feed to be isomerized being contacted with the catalyst described hereinbefore in a fixed bed at a temperature in the range of 80 to 330° C., preferably of 100 to 200° C., in the presence of hydrogen. The pressure in the isomerization reactor generally is in the range of 1 to 60 bar, preferably of 2 to 40 bar, with the LHSV ranging from 0.5 to 40 $h^{-1}$, preferably from 1 to 20 $h^{-1}$, and the ratio between the hydrogen and the feed being in the range of 0.005 to 10 N1/1, preferably in the range of 0.01 to 5 N1/1. As those skilled in the art will know, if so desired, a minute amount of a halogen-containing compound may be incorporated into the feed in order to extend the life of the catalyst. Thus, 0.001 to 1 wt. %, calculated as halogen, of a hydrogen halide, a halogen gas, or a halogenated hydrocarbon, such as carbon tetrachloride, chloroform, chloroethane, chloroisopropane, etc., may be added to the feed.

In addition, the catalyst prepared by the process according to the invention may be used for the alkylation of alkylatable aromatic or aliphatic hydrocarbons by contacting the compound to be alkylated with an alkylating agent at a suitable temperature and pressure in the presence of the catalyst obtained by the process according to the invention. Alkylating reactions are known to those skilled in the art and require no further elucidation here.

Other reactions in which the catalyst prepared by the process according to the invention may be used are the dimerization and oligomerization of olefins.

EXAMPLE 1

About 1000 g of gamma-alumina extrudates having a purity higher than 99.9% and an overall pore volume of 0.5 ml/g (determined by mercury porosimetry) were contacted for a period of 4 hours with about 2 kg of an aqueous solution containing 11.8 g of chloroplatinic acid (25% platinum), 26.7 g of 37%-hydrochloric acid, and 39.7 g of 65%-nitric acid. Next, the extrudates were dried at 120° C. for 16 hours and calcined at 550° C. for 1.5 hours. The platinum content of the calcined product was 0.29 wt. %, the chlorine content 0.9 wt. %.

306 g of the calcined product were transferred to a round-bottom flask, where 320 g of a 20 wt. %-ethyl aluminum dichloride solution in heptane were added to it. During the addition, the temperature rose from 31° C. to 54° C.; subsequently, it was increased to 80° C. The reaction period at 80° C. was one hour. During the reaction a nitrogen flow was passed over the catalyst (100 ml/min). Next, the liquid was drained from the round-bottom flask; any remaining liquid was evaporated at a temperature of 130° C. under a nitrogen flow of 1300 ml/min.

The product in the round-bottom flask was then heated to 640° C. in a 5% hydrogen-and 95% nitrogen flow (total flow: 2000 m/min). After one hour of activating at 640° C. using the same hydrogen/nitrogen flow, the product was cooled to room temperature to complete the preparation of the catalyst.

A small portion (10 g) of the catalyst was transferred to a test reactor with air being excluded. The temperature was then increased to 146° C. and a mixture of oil feed and hydrogen was passed over the catalyst. The hydrogen/oil feed molar ratio was 3, the pressure was 30 bar, and the space velocity was 4 g of oil per g of catalyst per hour. To the oil feed, composed of 42 wt. % of normal pentane, 48 wt. % of normal hexane, and 10 wt. % of cyclohexane, was added 300 ppm of Cl, in the form of $CCl_4$. After three hours of operating, the composition of the oil product was measured. This composition was used to calculate a $INC_5$ and a $INC_6$ number, in which the acronym IN stands for isomerization number, by means of the following formulae:

$$INC_5 = \frac{iC_5}{iC_5 + nC_5} \times 10$$

and, $$INC_6 = \frac{2.2\,DMB}{2.2\,DMB + 2.3\,DMB + 2MP + 3MP + nC6} \times 100$$

wherein the symbols iC5, nC5, 2.2 DMB, 2.3 DMB, 2 MP, 3 MP, and nC6 are concentrations in the oil product of:

iC5=isopentane
nC5=normal pentane
2.2 DMB=2,2 dimethyl butane
2.3 DMB=2,3 dimethyl butane
2 MP=2 methyl pentane
3 MP=3 methyl pentane
nC6=normal hexane In the experiment described above a $INC_5$ value of 56 and a $INC_6$ value of 19 were determined. The amount of cracking products (butane and lighter) was less than 0.3 wt. %.

EXAMPLE 2

300 g of high purity alumina extrudates containing 0.28 wt. % of Pt and 1.1 wt. % of chlorine and having a pore volume of 0.5 ml/g, which were prepared by a process analogous to that described in the first paragraph of Example 1, were transferred to a round-bottom flask. The extrudates in the flask were treated with 500 ml/min of 100% hydrogen for two hours at 400° C., after which they were cooled down to room temperature with nitrogen. 376 g of a solution of 20 wt. % ethyl aluminum dichloride in heptane were added to the flask. During the addition, the temperature rose to 42° C., subsequently it was increased to 85° C. The reaction mixture was kept at this temperature for a period of one hour. During the reaction a nitrogen flow was passed over the catalyst (100 ml/min). Next, the liquid was drained from the round-bottom flask; any remaining liquid was evaporated at a temperature of 130° C. under a nitrogen flow of 3000 ml/min. After drying, the product in the round-bottom flask was heated to 675° C. in a 5% hydrogen and 95% nitrogen flow (total flow: 2000 ml/min). After one hour of activating at 675° C. using the same hydrogen/nitrogen flow, the product was cooled to room temperature under 100% nitrogen to complete the preparation of the catalyst according to the invention.

A small portion (10 g) of the thus-prepared catalyst was transferred to a test reactor with air being excluded. The temperature was then increased to 155° C. and a mixture of oil feed and hydrogen was passed over the catalyst. The hydrogen/oil feed molar ratio was 0.1, the pressure was 31 bar, and the space velocity was 5 g of oil per g of catalyst per hour. To the feed, composed of n-butane, was added 100 ppm of $CCl_4$. After approximately 1000 minutes of operation, the composition of the effluent was determined. This composition was used to calculate a $INC_4$ number using the following formula:

$$INC_4 = \frac{iC_4}{iC_4 + nC_4} \times 100$$

It appeared that the $INC_4$ was 62.5.

EXAMPLE 3

300 g of high purity alumina extrudates containing 0.28 wt. % of Pt and 1.1 wt. % of chlorine and having a pore volume of 0.5 ml/g, which were prepared by a process analogous to that described in the first paragraph of Example 1, were transferred to a round-bottom flask. The extrudates in the flask were treated with 500 ml/min of 100% hydrogen for two hours at 400° C., after which they were cooled down to room temperature with nitrogen. 380 g of a solution of 20 wt. % ethyl aluminum dichloride in heptane were added to the flask. During the addition, the temperature rose from 28° C. to 50° C., subsequently it was increased to 85° C. The reaction mixture was kept at this temperature for a period of one hour. During the reaction a nitrogen flow was passed over the catalyst (100 ml/min). Next, the liquid was drained from the round-bottom flask; any remaining liquid was evaporated at a temperature of 130° C. under a nitrogen flow of 1300 ml/min. The product was then cooled down to room temperature. In this way, a comparative catalyst according to the teaching of GB Patent 1432639 was obtained, which contained 0.26 wt. % of Pt, and about 8 wt. % of Cl.

To obtain a catalyst according to the invention, the process for preparing the comparative catalyst according to GB Patent 1432639 above was repeated, except that the product was subjected to an additional activation step. After the removal of the remaining liquid by evaporation at a temperature of 130° C. under a nitrogen flow of 1300 ml/min, the product in the round-bottom flask was heated to 640° C. in a 5% hydrogen and 95% nitrogen flow (total flow: 2000 ml/min). After one hour of activating at 640° C. using the same hydrogen/nitrogen flow, the product was cooled to room temperature under 100% nitrogen to complete the preparation of the catalyst according to the invention.

Both the comparative catalyst according to GB Patent 1432639 and the catalyst according to the invention were subjected to the test procedure described in Example 1 above. After approximately 1000 minutes of operating, the composition of the oil product was measured. This composition was used to calculate a $INC_5$ and a $INC_6$ number. The test results are given in the following Table.

| Catalyst | $INC_5$ | $INC_6$ |
| --- | --- | --- |
| Catalyst according to GB 1432639 | 15.8 | 3.0 |
| Catalyst according to the invention | 61.9 | 21.8 |

From this table it appears that the catalyst according to the invention, which differs from the catalyst according to GB 1432639 only in that it has been subjected to a high-temperature treatment in the presence of hydrogen, shows a highly improved isomerization activity, as is evidenced by both a higher $INC_5$ and a higher $INC_6$.

EXAMPLE 4

250 g of high purity alumina extrudates containing 0.28 wt. % of Pt and 1.1 wt. % of chlorine and having a pore volume of 0.5 ml/g, which were prepared by a process analogous to that described in the first paragraph of Example 1, were transferred to a round-bottom flask. 280 g of a solution of 20 wt. % triethyl aluminum in heptane were added to the flask. During the addition, the temperature rose from 28° C. to 52° C., subsequently it was increased to 85° C. The reaction mixture was kept at this temperature for a period of one hour. During the reaction a nitrogen flow was passed over the catalyst (100 ml/min). Next, the liquid was drained from the round-bottom flask.

A flow of hydrochloric acid, hydrogen, and nitrogen was introduced. In 35 minutes, the HCl flow was increased from 120 ml/min to 720 ml/min. Within the same time frame, the nitrogen flow was decreased from 1600 ml/min to 0 ml/min, and the hydrogen flow from 200 ml/min to 72 ml/min. At that point in time, the temperature was 108° C. The catalyst then was heated to 250° C. in 35 minutes under a flow of 720 ml/min of HCl and 72 ml/min of hydrogen, and kept at that temperature for two hours. Then, the HCl flow was shut off and the hydrogen flow increased to 500 ml/min. The temperature was increased to 350° C. These conditions were maintained for one hour, after which the catalyst was cooled down to room temperature under 100% nitrogen. In this way, a comparative catalyst according to the teaching of GB Patent 952348 was obtained, which contained about 7.2 wt. % of Cl.

To obtain a catalyst according to the invention, 220 g of the catalyst according to GB Patent 952348 prepared above were heated in the round-bottom, flask to 640° C. in a 5% hydrogen and 95% nitrogen flow (total flow: 2000 ml/min). After one hour of activating at 640° C. using the same hydrogen/nitrogen flow, the product was cooled to room temperature under 100% nitrogen to complete the preparation of the catalyst according to the invention.

Both the comparative catalyst according to GB Patent 952348 and the catalyst according to the invention were subjected to the test procedure described in Example 1 above. After approximately 1000 minutes of operating, the composition of the oil product was measured. This composition was used to calculate a $INC_5$ and a $INC_6$ number for both experiments. The results thereof are given in the following Table.

| Catalyst | $INC_5$ | $INC_6$ |
|---|---|---|
| Catalyst according to GB Patent 952348 | 31.4 | 8.6 |
| Catalyst according to the invention | 51.2 | 15.2 |

From this table it appears that the catalyst according to the invention, which differs from the catalyst according to GB Patent 952348 only in that it has been subjected to a high-temperature treatment in the presence of hydrogen, shows an improved isomerization activity, as is evidenced by both a higher $INC_5$ and a higher $INC_6$.

What is claimed is:

1. A process for preparing an activated isomerization catalyst composition comprising the following steps:
   (a) preparing a composition comprising a Group VIII noble metal and an alumina carrier containing up to 20 wt % of other components,
   (b) optionally reducing the noble metal,
   (c) contacting the product of step (a) or (b) with a hydrocarbon-substituted aluminum compound, and
   (d) activating the product of step (c) by contacting the product of step (c) with a hydrogen-containing gas at a temperature above 500° C., with the proviso that at least when the hydrocarbon-substituted aluminum compound present in the catalyst composition is not a hydrocarbon-substituted aluminum halide, the catalyst composition to be activated is contacted with a halogen compound either prior to or during the activating step,
   wherein the activated isomerization catalyst contains at least 2.5 wt % halide, based on the total weight of the activated catalyst.

2. The process of claim 1, wherein the activated isomerization catalyst contains at least 3.0 wt % halide, based on the total weight of the activated catalyst.

3. The process of claim 1, wherein the activated isomerization catalyst contains at least 3.5 wt % halide, based on the total weight of the activated catalyst.

4. The process of claim 1, wherein the hydrocarbon-substituted aluminum compound present in the isomerization catalyst composition to be activated is a hydrocarbon-substituted aluminum halide.

5. The process of claim 4, wherein the hydrocarbon-substituted aluminum halide is a hydrocarbon-substituted aluminum chloride.

6. The process of claim 4, wherein the hydrocarbon-substituted aluminum halide is a compound of the formula $AlX_yR1_nR2_m$, wherein X is a halogen atom, R1 and R2 may be the same or different and are selected from alkyl groups and aryl groups having 1 to 12 carbon atoms, y has the value 1 or 2, and n and m have the value 0 or 1, with the sum of y, n, and m being 3.

7. The process of claim 1, wherein the hydrocarbon-substituted aluminum compound present in the isomerization catalyst composition satisfies the formula $AlR1R2R3$, wherein R1, R2, and R3 may be the same or different and are selected from alkyl groups or aryl groups having 1 to 12 carbon atoms.

8. The process of claim 7, wherein the isomerization catalyst composition comprising the hydrocarbon-substituted aluminum compound which is not a hydrocarbon-substituted aluminum halide is contacted with a halogen compound prior to the activation step being effected.

9. The process of claim 1, wherein the isomerization catalyst composition is activated using a hydrogen-containing gas which does not contain any halogen compounds.

10. The process of claim 1, wherein the isomerization catalyst composition is activated using a gas which in addition to hydrogen contains a halogen compound.

11. The process of claim 10, wherein the halogen compound is hydrogen chloride.

12. The process of claim 1, wherein the isomerization catalyst composition contains platinum as the Group VIII noble metal.

13. The activated isomerization catalyst composition prepared by the process of claim 1.

* * * * *

UNITED STATES PATENT AND TRADEMARK OFFICE
CERTIFICATE OF CORRECTION

PATENT NO. : 6,150,296
DATED : November 21, 2000
INVENTOR(S) : Jacobus J.L. Heinerman and Petrus J. Mangnus Page 1 of 1

It is certified that error appears in the above-identified patent and that said Letters Patent is hereby corrected as shown below:

Column 6,
Line 21, change "2000 m/min" to -- 2000 ml/min --.

Column 7,
Line 5, change "-of" to -- of --.

Signed and Sealed this

Twenty-first Day of May, 2002

*Attest:*

JAMES E. ROGAN
*Director of the United States Patent and Trademark Office*

*Attesting Officer*